United States Patent [19]

Corso, Jr.

[11] Patent Number: 5,601,539
[45] Date of Patent: Feb. 11, 1997

[54] MICROBORE CATHETER HAVING KINK-RESISTANT METALLIC TUBING

[75] Inventor: Philip P. Corso, Jr., Davie, Fla.

[73] Assignee: Cordis Corporation, Miami Lakes, Fla.

[21] Appl. No.: 506,669

[22] Filed: Jul. 25, 1995

Related U.S. Application Data

[63] Continuation of Ser. No. 147,134, Nov. 3, 1993, abandoned.

[51] Int. Cl.⁶ .................................................. A61M 25/00
[52] U.S. Cl. .................... 604/282; 604/264; 604/280; 604/49
[58] Field of Search ...................... 604/264, 280–282, 604/96, 49–53; 606/194; 148/402

[56] References Cited

U.S. PATENT DOCUMENTS

| | | |
|---|---|---|
| 3,620,212 | 11/1971 | Fannon et al. . |
| 3,753,700 | 8/1973 | Harrison et al. . |
| 3,786,806 | 1/1974 | Johnson et al. . |
| 3,890,977 | 6/1975 | Wilson . |
| 3,953,253 | 4/1976 | Clark ................................. 148/402 |
| 4,110,396 | 8/1978 | Reynolds ........................... 138/125 |
| 4,283,233 | 8/1981 | Goldstein et al. . |
| 4,411,655 | 10/1983 | Schreck ............................. 604/281 |
| 4,503,569 | 3/1985 | Dotter . |
| 4,565,589 | 1/1986 | Harrison ........................... 148/402 |
| 4,665,906 | 5/1987 | Jervis . |
| 4,740,253 | 4/1988 | Simpson et al. ................. 148/402 |
| 4,877,031 | 10/1989 | Conway et al. . |
| 4,894,100 | 1/1990 | Yamauchi et al. ............... 148/402 |
| 4,925,445 | 5/1990 | Sakamoto et al. . |
| 4,960,410 | 10/1990 | Pinchuk ............................. 604/280 |
| 4,969,890 | 11/1990 | Sugita et al. . |
| 4,998,917 | 3/1991 | Gaiser ................................. 606/194 |
| 4,998,923 | 3/1991 | Samson et al. .................... 606/194 |
| 5,047,045 | 9/1991 | Arney et al. ....................... 604/280 |
| 5,069,226 | 12/1991 | Yamauchi et al. . |
| 5,069,673 | 12/1991 | Shwab ................................. 604/280 |
| 5,346,505 | 9/1994 | Leopold ............................... 604/96 |
| 5,348,537 | 9/1994 | Wiesner et al. . |
| 5,397,305 | 3/1995 | Kawula et al. . |
| 5,484,409 | 1/1996 | Atkinson et al. . |

FOREIGN PATENT DOCUMENTS

| | | |
|---|---|---|
| 0141006 | 5/1985 | European Pat. Off. . |
| 0376132 | 7/1990 | European Pat. Off. . |

OTHER PUBLICATIONS

Shape Memory and Super–elasticity Effects in NiTi Alloys.

*Primary Examiner*—Mark Bockelman
*Attorney, Agent, or Firm*—Lockwood, Alex, Fitz-Gibbon & Cummings

[57] ABSTRACT

A catheter and procedure for its use are provided. The catheter includes an elongated proximal shaft that is made of flexible metallic tubing which is an alloy including nickel and titanium as the principal components. The elongated shaft is virtually kink-free when used, the use being at temperatures below the transition temperature or the temperature at which reversion to an austentic state is complete, the temperature being below warm-blooded body temperature. Preferably, a more atraumatic distal shaft is secured to the distal end of the elongated metallic tubing proximal shaft. During use, the catheter exhibits superior torsional strength, is virtually kink-free, and provides enhanced fluid flow due in large part to an exceptionally thin-walled and microbore characteristic of the metallic tubing.

17 Claims, 1 Drawing Sheet

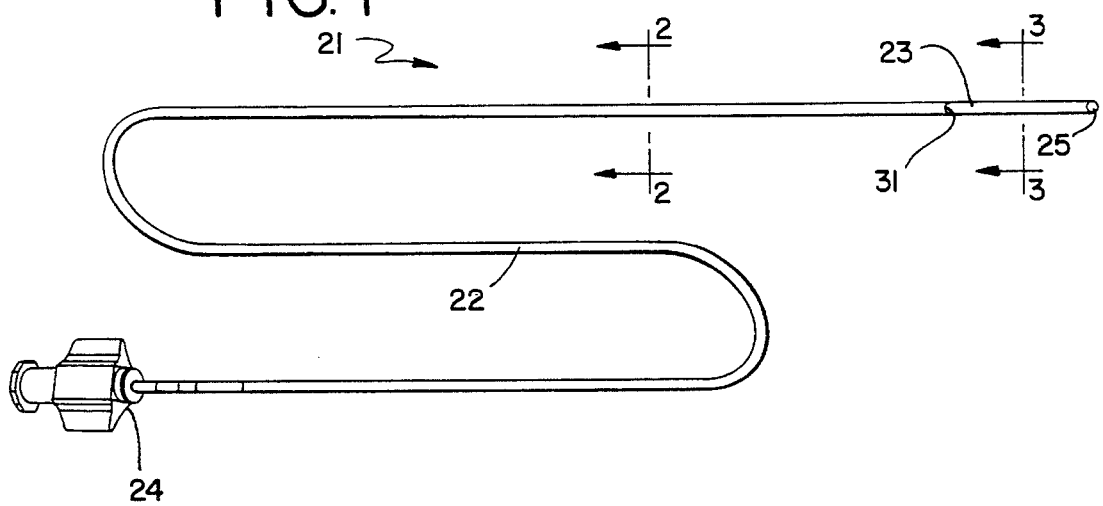
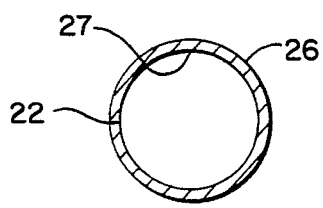 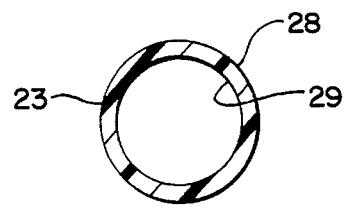
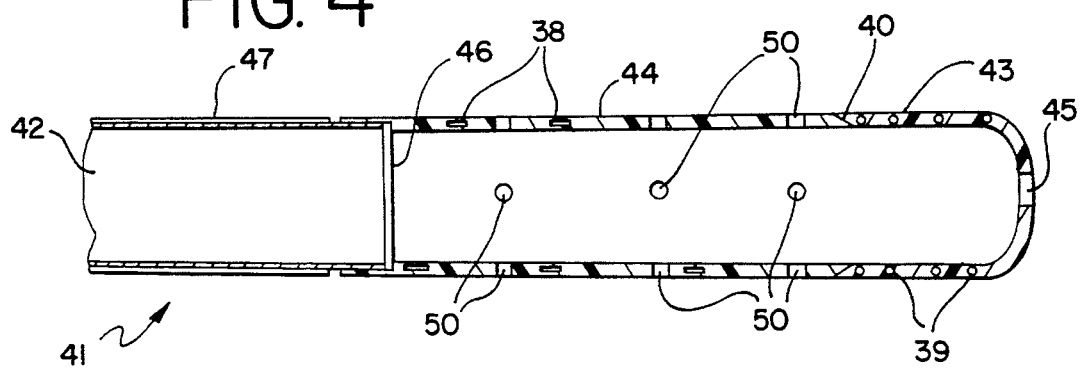

MICROBORE CATHETER HAVING KINK-RESISTANT METALLIC TUBING

This application is a continuation of application Ser. No. 147,134, filed Nov. 3, 1993.

DESCRIPTION

Background and Description of the Invention

The present invention generally relates to medical catheters that are particularly suitable for use as catheters having especially small diameter sizes. A primary component of the catheter is a highly kink-resistant shaft which provides an exceptional degree of pushability and provides a catheter that has a virtually kink-free design. At the same time, the kink-resistant shaft has an exceptionally thin wall thickness, especially when compared with typical polymeric catheter shafts. The kink-resistant shaft includes an elongated length of flexible metallic tubing which is an alloy including nickel and titanium as the principal components. Preferably, the catheter also includes a distal shaft made of a polymeric tubing.

Catheters for medical uses are provided in various shapes, sizes and configurations. With many catheters, diametrical sizing parameters are of particular importance. In many applications, the catheter must be capable of fitting within body passageways, such as blood vessels, which are narrow or of a particularly small diameter. Typically, there is also an incentive to provide an inner diameter that is as large as possible for a given outer diameter of the catheter so that maximum fluid flow through the catheter lumen is achieved. Catheters also typically need to have good torsional strength so that the catheter has the pushability or stiffness to pass through elongated vessels and be responsive to twisting and turning as is needed for proper catheter insertion.

At the same time, a catheter must have adequate flexibility so as to bend and move through curves within body passageways and the like. Some catheters achieve the requisite flexibility for use in tortuous passageways by using especially flexible materials or special constructions, but with the likelihood of developing kinks during use when bending and twisting operations must be carried out.

Catheter tubings have historically been made primarily of polymeric materials of various types. Polymers typically are deficient in strength properties. In those instances where thin-walled polymer tubings have been attempted for catheters that are particularly small in outer diameter but have a somewhat large bore or internal diameter, such thin-walled polymer tubing often exhibits kinking and is not particularly well-suited for exceptional torque control. When such a polymeric catheter kinks, the kink can appear to removed when the tubing is suitably straightened, but the sharp bending associated with a kink often is a location for the development of breaks or pin holes because the sharp bending has weakened the tubing at that location. Usually, attempts are made to design these types of potential problems out of a catheter by using a tubing having a wall thickness which resists kinking and which imparts an added degree of torsional rigidity. Other approaches add structural components such as braiding within the polymer wall. For example, however, attempts along these lines are not always overwhelming successes. Polymers have inherent strength limitations, and it is at times desirable to have a wall thickness that is not suitable for a particular catheter type.

Approaches have been suggested for utilizing so-called hypodermic tubing or hypotubes as catheter components. Hypotubes are typically made of stainless steel. The hypotube approach can be beneficial in providing a relatively thin-walled tubing having good torsional strength or stiffness. However, hypotubes are extremely susceptible to kinking, particularly if provided in a form thin enough to have adequate flexibility and wall thinness suitable for other needs of the catheter. Once a traditional metallic hypotube is maneuvered through a curve beyond its reasonable flexing capabilities, kinks will develop. Once developed, kinks in these types of metallic tubes cannot be removed by simple straightening procedures. Instead, a permanent dent or crease is formed in the wall of the tube. Kinks seriously debilitate the maneuverability of the tubing and render it a permanently imperfect device for following needed catheter introduction procedures.

It has been found that catheters in accordance with the present invention provide a unique combination of properties for catheter tubing by providing a high degree of pushability or torque control while being highly kink-resistant, all while incorporating a tubing that is advantageously thin-walled. The metallic tubing thus incorporated according to the invention provides an important combination of properties including good pushability and good torsional properties for steerability, together with exceptional flexibility, superelasticity, and the ability to be bent and rebent without kinking.

In summary, the present invention provides advantageous properties along these lines by a catheter which incorporates an elongated proximal shaft of flexible metallic tubing which is an alloy including nickel and titanium as the principal components. Preferably, the alloy has austentic properties that do not effect a shape change during normal temperatures to which the catheter is subjected during use. The elongated metallic alloy proximal shaft is combined with a polymeric distal shaft that has greater flexibility than the metallic proximal shaft while exhibiting enhanced atraumatic properties when compared with the proximal shaft.

It is a general object of this invention to provide an improved catheter having microbore characteristics.

Another object of the present invention is to provide an improved medical catheter which is suitable for use as a relatively large bore micro-catheter within extremely fine vessels, including cerebrospinal vessels, such as in the cerebrovascular system.

Another object of this invention is to provide an improved medical catheter which is of a virtually kink-free design while exhibiting exceptional pushability.

Another object of the present invention is to provide an improved catheter incorporating tubing made of alloys of nickel and titanium and to the use of such tubing during medical catheterization procedures whereby fluids are distributed within body passageways at maximized flow rates for a given outer diameter and without the danger of kinking during catheter maneuvering procedures.

Another object of this invention is to provide an improved catheter and catheterization procedure incorporating thin-walled metallic catheter tubing to effect increased injection pressures for a catheter of a given outer diameter.

These and other objects, features and advantages of this invention will be clearly understood through a consideration of the following detailed description.

BRIEF DESCRIPTION OF THE DRAWINGS

This invention will be further elucidated in the following description with reference to the drawings in which:

FIG. 1 is a generally perspective view of a catheter in accordance with the present invention;

FIG. 2 is a transverse cross-sectional view along the line 2—2 of FIG. 1;

FIG. 3 is a transverses cross-sectional view along the line 3—3 of FIG. 1; and

FIG. 4 is a longitudinal cross-sectional view of a distal portion of a catheter in accordance with the present invention and which illustrates various alternate embodiments and features.

DESCRIPTION OF THE PARTICULAR EMBODIMENTS

A catheter in accordance with this invention, generally designated as 21, is illustrated in FIG. 1. Included is a proximal shaft 22 and a distal shaft 23 secured thereto. Also shown is a hub unit 24 secured to the distal end of the catheter 21. Hub unit 24 is representative of a number of distal end members or assemblies of generally known construction and provided for facilitating any number of catheter procedures, such as fluid injection and/or passage of a guidewire or other item through the lumen of the catheter. In a typical catheter such as that illustrated in FIG. 1, an end opening 25 is provided at the distal tip of the catheter for passage of fluids, members or devices out of the distal end of the catheter.

In an important aspect of the invention, the proximal shaft 22 illustrated in FIG. 1 and FIG. 2 is a metallic alloy tube having an outer surface 26, a lumen wall 27, and a wall thickness therebetween which is especially thin. The thin-wall characteristic of the proximal shaft 22 is illustrated by comparing it with the wall thickness of the polymeric distal shaft 23 that is illustrated in FIGS. 3 and 4. In this illustrated embodiment, the outer surface 28 of the distal shaft 23 is of the same diameter as the outer surface 26 of the metal alloy proximal shaft 22, but the diameter of its lumen wall 29 is noticeably less than the diameter of lumen wall 27 of the metal alloy proximal shaft 22. Accordingly, it will be understood that the thin-wall construction of proximal shaft provides a large bore or lumen for facilitating fluid passage therethrough, which is important for a successful microbore catheter.

It will be appreciated that the invention is not limited to catheters in which the distal shaft has a wall thickness which is thicker than that of the proximal shaft. In fact, the exceptional pushability and torsional control afforded by the proximal shaft permits a very thin-walled distal shaft to be utilized, including one that is at least as thin as the metallic proximal shaft to thereby provide the large lumen or microbore characteristic throughout the length of the catheter.

Catheters according to the present invention are further characterized by the substantial flexibility and malleability, accompanied by good torque control properties and excellent kink-resistance of the metallic alloy proximal shaft 22. The material out of which the proximal shaft is made is an alloy including nickel and titanium. These are generally categorized as Nitinol alloys. Preferably, these nickel and titanium-containing alloys are selected to have austentic properties that do not effect a shape change during normal temperatures to which the catheter is subjected during use. Alloys of this type generally exhibit superelasticity. These alloys are particularly useful for the catheters of the present invention. If they should be bent beyond the normally accepted bendability to which the tubing can be subjected, they will readily "un-bend" rather than form a kink at the bend location. Catheter or guidewire tubes made of stainless steel, for example, exhibit kinking when bent and straightened, to the extent that it typically is not possible to fully eliminate a kink in such metallic tubes without leaving a dent or crease that interferes with proper and responsive insertion procedures.

It has been found that the properties characteristic of this invention are achieved when using metal alloy proximal shafts as discussed herein made with alloys of nickel and titanium and which exhibit an austentic temperature greater than about 10° C. and not greater than about 20° C. They can exhibit superelasticity, but they do not undergo temperature-induced shape changes normally associated with shape memory alloys when they are subjected to the temperatures which catheters encounter during normal use, including warm-blooded body temperatures and room temperature. In addition, if the metal alloy has an $A_f$ temperature above about 20° C., its superelastic characteristic which facilitates bending without kinking may be diminished. Catheters made in accordance with the present invention exhibit adequate bending freedom and exceptional kink-resistance. Not only are they flexible, but they also exhibit very good steerability and they torque extremely well during insertion.

Catheters according to the present invention can be reused if desired and appropriate. If the catheter bends during movement through a path within a vessel, the bend or position within the body can be modified, and the catheter can be maneuvered into and through another path developing a different bend. This is due in part to the avoidance of kinking and the ability of even the metal alloy proximal shaft of the catheter to return to its original shape after bending as may be required for many insertion techniques.

Micro-sizing with exceptionally large relative bore sizes and superelasticity, which are characteristic of the catheters of this invention, make them especially suitable for delicate applications within small and highly branched vessels, even such as those within the cerebrovascular system which has very tortuous and typically very narrow passageways. Micro-bore catheters made according to the present invention have the characteristics which render them operational within the cerebrovascular system; they are able to access locations therein which cannot be readily accessed by other types of catheters having the relatively large bore sizes made possible by the present invention.

A joint 31 is presented at the location where the distal end of proximal shaft 22 is secured to the proximal end of the distal shaft 23. Joint 31 may take the form of a medical grade adhesive or cement, a weld, a mechanical attachment, or a combination of generally known attachment procedures. A typical cement is a medical grade adhesive and can include an epoxy adhesive or the like.

The distal shaft portion or portions of the invention are made of any suitable polymeric material for use as a catheter. The polymeric material will be more atraumatic than the metallic alloy shaft. The material is also suitable for ready formation of passageways between the inner lumen of the catheter and the exterior of the catheter. Exemplary polymers include most thermoplastic materials such as polyethylene, polyvinylchloride and the like. Other suitable polymers include silicone rubbers, polyurethanes and virtually any medical grade polymer that presents a reasonable atraumatic lead or tip component for the catheter. Polymeric distal shaft can be simply extruded as a tube or can utilize added structural components such as those of braided polymer matrix structures that exhibit good torque properties and kink-resistance, as well as coiled polymer matrix structures that offer limited torque control but exceptional kink-resistance and flexibility. In this regard, braids 38 and coil 39 are illustrated in FIG. 4.

FIG. 4 also shows features which can be incorporated into alternate embodiments of the present invention. Illustrated catheter 41 includes metallic alloy proximal shaft 22 and a plurality of distal shafts 43, 44 secured together at a joint 40. Shafts 43, 44 will typically be made of polymeric material as generally discussed herein. Such shafts 43, 44 may be made of polymers or tube assemblies possessing different strengths and flexibilities to impart various control parameters to the catheter. Also shown is an end opening 45 and a plurality of side holes 50 for enhancing fluid delivery through the catheter.

A technique for assembly of the polymeric shaft to the metallic alloy proximal shaft is also illustrated in FIG. 4. An annular recess 46 is provided within the polymeric tubing in order to facilitate reception of the proximal shaft 42 with respect to the distal shaft. Also illustrated is a coating or covering 47 onto the metallic alloy proximal shaft 42. Typically, any such coating or covering 47 is made of lubricious material. Illustrative lubricious materials include a Teflon sleeve, a spray coating of lubricious material, a dip coating of silicone, or other similar treatments or coatings.

Elongated proximal shaft 22, 42 is made of an alloy including nickel and titanium in an approximate 50:50 mixture and having a raw state temperature typically greater than about 10° C. and not greater than about 20° C. as the $A_f$ temperature range. Lower $A_f$ temperatures are contemplated, it being important that this transition temperature is well below body temperature. It is generally unnecessary and undesirable for the shape memory properties of the alloy to exhibit themselves during use within warm-blooded environments.

The tensile strength of a typical alloy suitable for use as the proximal shaft is a minimum of about 150 KPSI, preferably at least about 180 KPSI. In some instances it can be desirable to have the metallic alloy proximal shaft exhibit differing stiffness properties along its length. For example, one portion could be cryogenically treated while the rest of the proximal tube is not so treated. The same approach can be used by heating or annealing only a selected length of the metallic alloy proximal shaft. In addition, catheter sizes will vary with the intended use of the catheter, with smaller sizes being of a type suitable for use within the cerebrovascular system, for example.

Typically, the metal alloy of the flexible proximal shaft is substantially exclusively nickel and titanium in substantially equal weight proportions. A preferred blend of the metal alloy contains between about 49.5 and about 50.5 weight percent, plus or minus 1 weight percent, of nickel and of titanium. A preferred material is 99 weight percent pure nickel and titanium. Preferably, other than trace impurities, the metallic alloy tubing need not contain any additional metals such as iron, copper or aluminum, although these can be included provided the properties discussed herein, particularly kink-resistance, are not compromised.

It will be understand that the embodiments of the present invention which have been described are illustrative of some of the applications of the principles of the present invention. Various modifications may be made by those skilled in the art without departing from the true spirit and scope of the invention.

I claim:

1. A microbore cerebrovascular catheter having enhanced kink-resistance, comprising:

an elongated proximal shaft defining the body of the microbore cerebrovascular catheter, said proximal shaft being a length of flexible metallic tubing to provide a flexible proximal shaft having a proximal end and a distal end, said flexible metallic tubing being a metallic alloy including nickel and titanium as the principal components, said nickel and titanium being in an approximate 50:50 mixture;

a hub member secured to said proximal end of the elongated proximal shaft;

a distal shaft in direct operative securement to said distal end of the elongated proximal shaft such that fluids pass between said proximal and distal shafts, said distal shaft being a polymeric tubing, said distal shaft being the distalmost component of the catheter and having an aperture through a wall portion thereof for passage of fluids from said proximal shaft and therethrough to a patient's tissue; and said elongated proximal shaft flexible metallic tubing is kink-resistant and has greater torsional strength than does said distal shaft polymeric tubing, said metallic alloy of said proximal shaft has austentic properties selected to substantially preclude temperature-induced shape changes during use and at temperatures above its $A_f$ temperature, at which reversion to an austentic state is complete, and said kink-resistant flexible proximal shaft is readily bendable from an original configuration to another configuration without kinking that is experienced by a substantially identically shaped and sized shaft which is made of stainless steel, including returning to the original configuration without leaving a crease therein.

2. The catheter in accordance with claim 1, wherein said $A_f$ temperature is equal to or greater than about 10° C.

3. The catheter in accordance with claim 1, wherein said proximal shaft is composed of a metallic alloy that is substantially exclusively nickel and titanium in substantially equal weight proportions.

4. The catheter in accordance with claim 1, further including a polymeric coating generally along the length of the proximal shaft, said coating having lubricious properties.

5. The catheter in accordance with claim 1, wherein said distal shaft is a braided polymer matrix tube.

6. The catheter in accordance with claim 1, wherein said distal shaft is a polymer matrix of a thin polymer tubular sheath supported by a helical coil.

7. The catheter in accordance with claim 1, wherein said distal shaft includes an intermediate shaft portion comprising a proximal portion of said distal shaft which effects said direct operative securement of said proximal shaft and distal shaft.

8. The catheter in accordance with claim 1, further including an annular recess at the distal end of said elongated proximal shaft, and said distal shaft is secured to said proximal shaft at said annular recess.

9. The catheter in accordance with claim 1, wherein said proximal shaft has a varied stiffness section along its length.

10. The catheter in accordance with claim 9, wherein a portion of said proximal shaft had been subjected to cryogenic treatment to provide said varied stiffness section.

11. The catheter in accordance with claim 9, wherein a portion of said proximal shaft had been subjected to heat treatment to provide said varied stiffness section.

12. The catheter in accordance with claim 1, wherein said $A_f$ temperature of the metallic alloy is not greater than about 20° C.

13. A cerebrovascular catheter having a microbore and having enhanced kink-resistance, comprising:

an elongated proximal shaft, said proximal shaft being a length of flexible metallic tubing to provide a flexible proximal shaft having a proximal end and a distal end, said flexible metallic tubing being a metallic alloy including nickel and titanium as the principal components, said nickel and titanium being in an approximate 50:50 mixture, said flexible metallic tubing having an outer diameter and a microbore lumen which has a maximized inner diameter with respect to its said outer diameter;

said metallic alloy has austenic properties selected to substantially preclude temperature-induced shape changes during use and at temperatures above its $A_f$ temperature, said $A_f$ temperature being not greater than about 20° C.;

a distal shaft secured directly to said distal end of the elongated proximal shaft such that fluids pass directly between said proximal and distal shafts, said distal shaft being a polymeric tubing, said distal shaft being the distalmost portion of the catheter and having an aperture through a wall portion thereof for passage of fluids from said proximal shaft and therethrough to a patient's tissue; and said elongated proximal shaft flexible metallic tubing is kink-resistant and has greater torsional strength than does said distal shaft polymeric tubing, and said elongated flexible proximal shaft is kink-resistant by being readily bendable from an original configuration to another configuration without kinking that is experienced by stainless steel tubes, including returning to the original configuration without kinking.

14. A cerebrospinal catheterization procedure, comprising the steps of:

providing a microbore cerebrospinal catheter having enhanced kink-resistance and which includes an elongated proximal shaft catheter body made of a flexible metallic tubing being an alloy including nickel and titanium as the primary components, said nickel and titanium being in an approximate 50:50 mixture, the proximal shaft having a distal shaft at its distal end, the distal shaft being a polymeric tubing which is distalmost on the catheter and having an aperture through a wall portion thereof;

inserting the medical catheter, using the distal shaft as the leading end, into a cerebrospinal vessel;

pushing the medical catheter through the cerebrospinal vessel while precluding temperature-induced shape changes, which pushing step includes maintaining the metallic proximal shaft at a temperature below its transition temperature and bending the flexible metallic proximal shaft while avoiding kinking thereof, until the distal shaft is at a treatment location in communication with the cerebrospinal vessel; and treating at the treatment location after the pushing step has been completed, said treating step including passing a fluid through a continuous lumen defined by said proximal shaft and distal shaft and through the aperture of the distal shaft.

15. The procedure in accordance with claim 14, wherein said providing step includes defining a microbore lumen through at least said proximal shaft by maximizing its lumen diameter with respect to its outer diameter, and said treating step includes flowing a fluid through the microbore lumen.

16. The procedure in accordance with claim 14, wherein said treating step includes passing a wire-like device through the microbore lumen.

17. A microbore cerebrovascular catheter having enhanced kink-resistance, comprising:

an elongated proximal shaft defining the body of the microbore cerebrovascular catheter, said proximal shaft being a length of flexible metallic tubing to provide a flexible proximal shaft having a proximal end and a distal end, said flexible metallic tubing being a metallic alloy including nickel and titanium as the principal components, wherein the weight percent of nickel is between about 49.5 and about 50.5 weight percent, and the weight percent of titanium is between about 49.5 and about 50.5 weight percent, based upon the total weight percent of the metallic alloy;

a hub member secured to said proximal end of the elongated proximal shaft;

a distal shaft in direct operative securement to said distal end of the elongated proximal shaft such that fluids pass between said proximal and distal shafts, said distal shaft being a polymeric tubing, said distal shaft having an aperture through a wall portion thereof for passage of fluids from said proximal shaft and therethrough to a patient's tissue; and said elongated proximal shaft flexible metallic tubing is kink-resistant and has greater torsional strength than does said distal shaft polymeric tubing, said metallic alloy of said proximal shaft has austenic properties selected to substantially preclude temperature-induced shape changes at temperatures above its $A_f$ temperature, at which reversion to an austenic state is complete, and said kink-resistant flexible proximal shaft is readily bendable from an original configuration to another configuration without kinking that is experienced by a substantially identically shaped and sized shaft which is made of stainless steel, including returning to the original configuration without leaving a crease therein.

\* \* \* \* \*

UNITED STATES PATENT AND TRADEMARK OFFICE
CERTIFICATE OF CORRECTION

PATENT NO.  : 5,601,539
DATED       : February 11, 1997
INVENTOR(S) : Philip P. Corso, Jr.

It is certified that error appears in the above-indentified patent and that said Letters Patent is hereby corrected as shown below:

Title page, "Attorney, Agent, or Firm", delete "Fitz-Gibbon" and insert ---FitzGibbon---.
Col. 1, line 54, "to removed" should read ---to be removed---.
Col. 3, line 5, "transverses" should read ---transverse---.
Col. 5, line 59, delete "understand" and insert ---understood---.

Signed and Sealed this

Twenty-eighth Day of July, 1998

Attest:

BRUCE LEHMAN

Attesting Officer    Commissioner of Patents and Trademarks